United States Patent [19]

Schaefer et al.

[11] Patent Number: 5,569,774
[45] Date of Patent: Oct. 29, 1996

[54] PROCESS FOR THE PREPARATION OF CHLORINE-SUBSTITUTED OLEFINS

[75] Inventors: Bernd Schaefer, Dierbach; Irene Troetsch-Schaller, Frankenthal, both of Germany

[73] Assignee: BASF Aktiengesellschaft, Ludwigshafen, Germany

[21] Appl. No.: 307,659

[22] PCT Filed: Mar. 13, 1993

[86] PCT No.: PCT/EP93/00586

§ 371 Date: Sep. 20, 1994

§ 102(e) Date: Sep. 20, 1994

[87] PCT Pub. No.: WO93/19034

PCT Pub. Date: Sep. 30, 1993

[30] Foreign Application Priority Data

Mar. 24, 1992 [DE] Germany .................. 42 09 497.6

[51] Int. Cl.$^6$ ............................................. C07D 303/38
[52] U.S. Cl. .................. 549/548; 549/550; 549/549; 546/336; 546/346; 560/20; 558/250; 558/257; 564/160
[58] Field of Search ................... 549/550, 548, 549/549; 546/336, 346; 560/20; 558/250, 257; 564/166

[56] References Cited

U.S. PATENT DOCUMENTS 5,198,557  3/1993  Giordano et al. ..................... 549/513

FOREIGN PATENT DOCUMENTS 1096899  1/1961  Germany .
1503775  3/1978  United Kingdom .

OTHER PUBLICATIONS

J. March, Adv. Org. Chem., Auckland, 2nd Ed., 1977, p. 739ff.
G. Wittig et al., Liebigs Ann. Chem., 44, p. 580 (1953).
G. Markl, Chem. Ber., 94, p. 2996 (1961).
Horner et al., Chem. Ber., 91, p. 61, (1958).
Horner et al., Chem. Ber., 92, p. 2499 (1959).
McKenna et al., J. Org. Chem., 51, p. 5467 (1986).
Ziegenbein et al., Chem. Ber., 95, p. 2976 (1962).
Newman et al., Org. React., 5, p. 413 (1949).

Primary Examiner—Samuel Barts
Attorney, Agent, or Firm—Keil & Weinkauf

[57] ABSTRACT

Chlorine-substituted olefins I

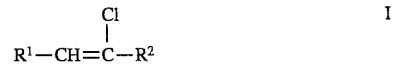

($R^1$=organic radical; $R^2$=—CN, —CO—$R^3$, —CO—S—$R^3$, —CO—O—$R^3$ —CO—N($R^4$,$R^5$); $R^3$=organic radical; $R^4$, $R^5$=H, organic radical)
are prepared by reacting oxiranes II

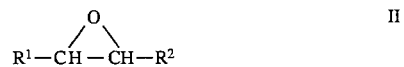

in the presence of a carboxamide (IIIa) or of a lactam (IIIb) in liquid phase with a chlorinating agent (IV). The products I are important intermediates for dyes, drugs and crop protection agents.

6 Claims, No Drawings

PROCESS FOR THE PREPARATION OF CHLORINE-SUBSTITUTED OLEFINS

This application was filed under USC 371 from the application PCT/EP 93/00586 filed Mar. 13, 1993 and published as WO93/19034 Sep. 30, 1993.

DESCRIPTION

The present invention relates to a novel process for preparing chlorine-substituted olefins of the general formula I

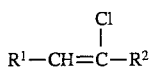

where $R^1$ is a C-organic radical and $R^2$ is one of the following groups: —CN, —CO—$R^3$, —CO—S—$R^3$, —CO—O—$R^3$ or —CO—$NR^4R^5$, where $R^3$ is a C-organic radical and $R^4$ and $R^5$ are each hydrogen or a C-organic radical.

Several methods are known for preparing α-chlorocinnamic esters as compounds I ($R^1$=phenyl; $R^2$=—$COOR^3$) but are unsatisfactory in various respects. Thus, it is possible first to add chlorine on to the double bond of the appropriate cinnamic ester and to eliminate hydrogen chloride from the α,β-dichlorinated 2-phenylpropionic esters (cf. for example, J. March, Advanced Organic Chemistry, McGraw Hill International Book Company, Aukland, 2nd ed., 1977, pages 739 et seq.). The disadvantage of this is that the selectivity of the reaction is poor.

Another method comprises reacting benzaldehyde (or a substituted benzaldehyde) with a) a phosphonium salt providing the moiety —CH(Cl)—$R^2$ by the Wittig method (G. Wittig, G. Geisler, Liebigs Ann. Chem. 44 (1953) 580 and G. Märkl, Chem. Ber. 94 (1961) 2996) or b) a corresponding monochlorinated phosphonoacetic ester by the Horner method (Horner, Hoffmann, Wippel, Chem. Ber. 91 (1958) 61; Horner, Hoffmann, Wippel, Klahre, Chem. Ber. 92 (1959) 2499 and McKenna, Khawli, J. Org. Chem. 51 (1986) 5467).

However, this procedure has disadvantages, not least in respect of technical difficulties.

It is furthermore known that the action of phosgene, phosphorus oxychloride, or phosphorus trichloride or pentachloride on oxiranes of the formula II'

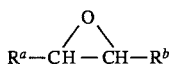

where $R^a$ and $R^b$ are each hydrogen, alkyl or phenyl or together are a carbocyclic ring, inter alia in excess dimethylformamide, results in 1,2-dichloro compounds (W. Ziegenbein, K. -H. Hornung, Chem. Ber. 95 (1962) 2976).

In accordance with the teaching of DE-A 10 96 899 the reaction of aliphatic or cycloaliphatic 1,2-epoxides, which may carry aryl or aralkyl substituents, with adducts of phosphorus oxychloride or phosgene and an N,N-dialkylamide and subsequent hydrolysis yields 1-acyloxy-2-chloroalkyl derivatives of alkanes or cycloalkanes.

It was an object of the present invention to provide a simple and industrially economic method starting from low-cost compounds which are easy to manipulate industrially for preparing the chlorine-substituted olefins I.

Accordingly, we have found that this object is achieved by a process for preparing chlorine-substituted olefins of the formula I, which comprises reacting an oxirane of the formula II

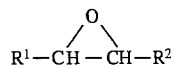

in the presence of a carboxamide (IIIa) or of a lactam (IIIb) in liquid phase with a chlorinating agent (IV).

We have also found novel oxiranes of the general formula IIa

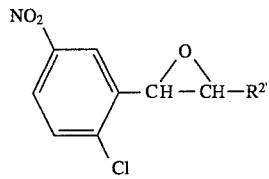

where $R^{2'}$ is cyano, $C_1$–$C_6$-alkylcarbonyl, $C_1$–$C_6$-alkoxycarbonyl or $C_1$–$C_6$-alkylthiocarbonyl.

The oxiranes of the formula II used as starting materials can be prepared by methods known per se (e.g. M. S. Newman, B. J. Magerlein, Org. React. 5 (1949) 413).

The novel oxiranes IIa are preferably obtained by reacting 2-chloro-5-nitrobenzaldehyde with a derivative of the formula L—$CH_2$—$R^{2'}$ where L is a nucleophilic leaving group, especially chlorine.

The reaction is carried out in an inert solvent or diluent in the presence of a strong base, for example an alkali metal alcoholate such as sodium methylate.

Particularly suitable solvents or diluents are lower alcohols such as methanol, ethanol and isopropanol. It is expedient to use the alcohol whose alcoholate comprises the base.

The reaction is generally carried out at from 0° to 40° C.

As a rule, the reaction is carried out under atmospheric pressure or under the autogenous pressure of the solvent used.

The chlorination according to the invention of the oxiranes II is carried out in the presence of a carboxamide or of a lactam, and examples of compounds which have proven particularly suitable are those of the formula IIIa

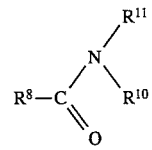

where the substituents have the following meaning:

$R^8$ is hydrogen, $C_1$–$C_6$-alkyl or phenyl and $R^{11}$ and $R^{10}$ are each $C_1$–$C_6$-alkyl or phenyl or $R^{11}$ and $R^{10}$ form, together with the common nitrogen atom, pyrrolidinyl, piperidinyl or morpholinyl; and of the formula IIIb

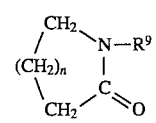

where n is 0, 1 or 2 and $R^9$ is $C_1$–$C_6$-alkyl or phenyl.

Present knowledge indicates that N,N-dimethylformamide, N-formylmorpholine, N-formylpiperidine, N-methyl-N-phenylformamide and N-methylpyrrolidone are particularly advantageous; dimethylformamide is very particularly preferred.

Suitable chlorinating agents are principally Vilsmeier salts or non-oxidizing chlorinating agents, ie. for example sulfuryl chloride, thionyl chloride, acetyl chloride, benzoyl chloride, pivaloyl chloride, bis(trichloromethyl) carbonate, oxalyl dichloride, phosphorus oxychloride, phosphorus trichloride, phosphorus pentachloride, methanesulfonyl chloride, chlorosulfonic acid, phosgene or trichloromethyl chloroformate (cf. also H. Eilingsfeld, M. Seefelder, H. Weidinger, Chem. Ber. 96 (1963) 2691; C. Jutz, Advances in Org. Chem. 9 (1976) 225; M. Grdinic, V. Hahn, J. Org. Chem. 30 (1965) 2381; H. Eilingsfeld, M. Seefelder, H. Weidinger, Angew. Chem. 72 (1960) 836).

An advantageous embodiment of the process comprises first preparing from the carboxamide (IIIa) or lactam (IIIb) the corresponding Vilsmeier salt (IVa or IVb) with a suitable non-oxidizing chlorinating agent, in particular with thionyl chloride, acetyl chloride, benzoyl chloride, oxalyl dichloride, phosphorus oxychloride, phosphorus trichloride, phosphorus pentachloride, chlorosulfonic acid, phosgene or trichloromethyl chloroformate, and reacting the resulting solution, which also contains excess carboxamide (IIIa) or lactam (IIIb), with the oxirane II:

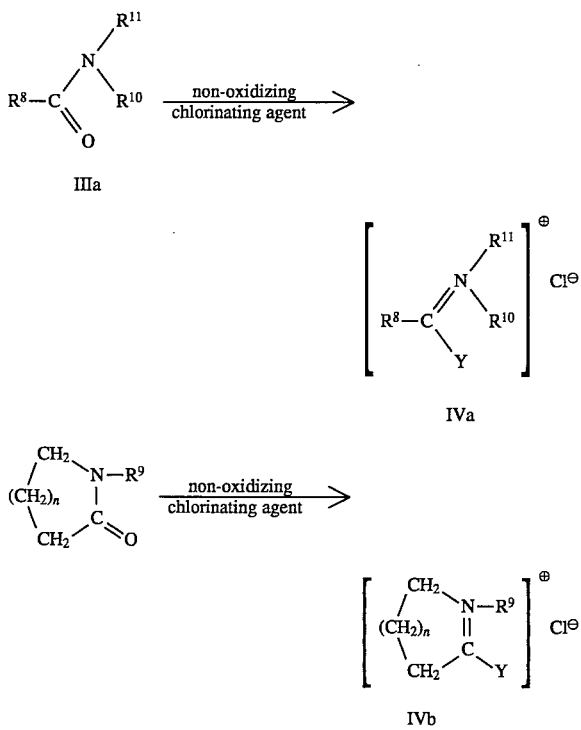

Y depends on the chlorinating agent used and is, in particular, chlorine, —OSOCl, —O—CO—CH$_3$, —O—CO-phenyl, —OPO(Cl)$_2$, —OP(Cl)$_2$ or —OP(Cl)$_4$.

Since the sequence of addition of the reactants normally has no effect on the product formation, it is immaterial whether the oxirane II is mixed with the carboxamide or lactam before or after addition of the chlorinating agent.

On the other hand, however, the Vilsmeier salt can also be isolated and purified after preparation, and only then be reacted with the oxirane II, in which case it is also possible to use a carboxamide or lactam other than that used to prepare the Vilsmeier salt.

If the thermal stability of the Vilsmeier salts is inadequate it may be advantageous first to saturate the carboxamide (IIIa) or lactam (IIIb) with hydrogen chloride and then to introduce the Vilsmeier salt (IVa or IVb) and the oxirane II.

It is additionally possible to improve the solubility of the reactants by adding an inert solvent or diluent which is inert under the chlorination conditions.

Suitable inert solvents for this purpose are petroleum ether, aromatic hydrocarbons such as toluene and o-, m- and p-xylene, chlorohydrocarbons such as dichloromethane, trichloromethane, tetrachloromethane, 1,1,1-trichloroethane and 1,2-dichloroethane or aromatic halohydrocarbons such as chlorobenzene.

However, it is preferable to carry out the reaction in a carboxamide (IIIa) or lactam (IIIb) without added solvent.

The amount of carboxamide or lactam, and inert solvent where used, should be such that at least some of the reactants dissolve.

It is advantageous to use approximately stoichiometric amounts of chlorinating agent and oxirane II. To avoid by-products it may, however, be advantageous to terminate the reaction before conversion is complete. In this case less than the stoichiometric amount of chlorinating agent, up to about 10 mol %, is used.

The optimal temperature for the reaction depends on the reactants used and is generally from about 0° to 150° C., preferably from 20° to 100° C.

The reaction is not recognizably dependent on the pressure so that it is advantageously carried out under atmospheric pressure. However, if the reactants are volatile (e.g. phosgene) it may also be advisable to increase the pressure up to about 20 bar, preferably up to 6 bar.

The reaction conditions are expediently maintained until oxirane II is no longer detectable in the reaction mixture (e.g. by thin-layer chromatography, high-pressure liquid chromatography or gas chromatography).

Work-up to give the final product is, as a rule, then carried out by conventional processes such as distillation, filtration, centrifugation or by adding water and subsequently extracting.

The process according to the invention should be carried out batchwise, e.g. in a stirred reactor. However, the simplicity of the process provides the advantage that it can also be carried out continuously, for example using a reaction pipe or a cascade of stirred reactors.

The crude products obtained can be purified if required, e.g. by crystallization, rectification or by chromatographic methods.

The products I are generally obtained as a mixture of the cis and trans isomers (relative to the olefinic double bond). The chlorination according to the invention of an optically active oxirane II which contains one of the two isomers in excess results in mixtures of cis and trans isomers I in which one configuration likewise predominates.

In view of the required products I, the following substituents $R^1$ and $R^2$ are particularly important:

$R^1$ an aromatic or heteroaromatic radical, in particular phenyl or pyridyl, both of which can be unsubstituted or carry one to three substituents selected from a group comprising fluorine, chlorine, bromine, nitro or an organic radical which has 1–12 carbons and, if required, can
  a) contain an oxygen or sulfur atom and/or
  b) be partially or completely halogenated;

$R^2$—CN or —CO—$R^3$ where $R^3$ is a C-organic radical with 1–12 carbons.

Examples of C-organic radicals with 1–12 carbons are the following groups:

— a branched or unbranched $C_1$–$C_6$-alkyl group which can also carry one or two $C_1$–$C_4$-alkoxy radicals, preferably methoxy and ethoxy, and/or $C_1$–$C_4$-alkylthio radicals, preferably methylthio;

— a cyclopropyl, cyclobutyl, cyclopentyl or cyclohexyl group;

— a $C_3$–$C_6$-alkenyl group, preferably 2-propenyl and 2-butenyl;

— a $C_3$–$C_6$-alkynyl group, preferably 2-propynyl and 2-butynyl;

— a $C_1$–$C_4$-alkoxy group, preferably methoxy and ethoxy;

— a $C_1$–$C_4$-alkythio group;

— an aryl group, in particular the phenyl group, a $C_1$–$C_4$-alkylphenyl group such as o-, m- or p-tolyl, a $C_1$–$C_4$-alkoxyphenyl group such as o-, m- or p-methoxyphenyl, a halophenyl group such as o-, m- or p-fluorophenyl, o-, m- or p-chlorophenyl and o-, m- or p-bromophenyl, and the o-, m- or p-nitrophenyl, o-, m- or p-trifluoromethylphenyl or o-, m- or p-biphenylyl group.

In view of the secondary products, which are mostly α-chlorinated cinnamic esters of the formula V

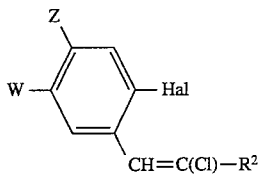

where Hal is fluorine, chlorine or bromine,

Z is hydrogen, fluorine, chlorine or bromine and

W is one of the following heterocyclic radicals:

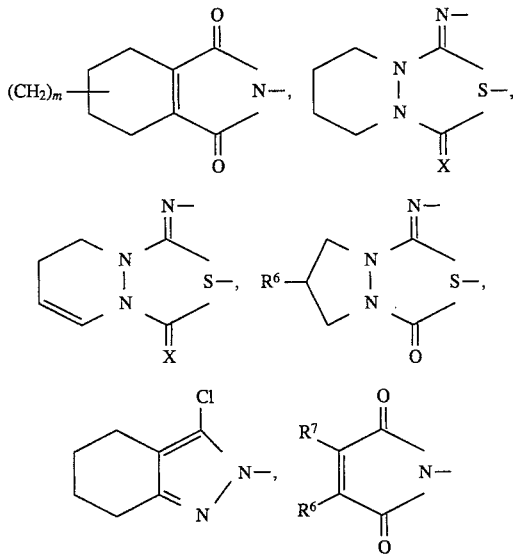

(m=0 or 1; X=oxygen or sulfur; $R^6$, $R^7$=hydrogen or $C_1$–$C_4$-alkyl)

$R^1$ is particularly preferably mono- or dichlorinated meta-anilino and $R^2$ is cyano, $C_1$–$C_6$-alkylcarbonyl or $C_1$–$C_6$-alkoxycarbonyl.

The collective terms used in the definition of the substituents:

— halogen,

— $C_1$–$C_6$-alkyl, $C_1$–$C_4$-alkyl, $C_1$–$C_4$-alkoxy, $C_1$–$C_4$-alkylthio, — $C_3$–$C_6$-alkenyl, $C_3$–$C_6$-alkynyl, $C_3$–$C_6$-alkynyloxy, — $C_1$–$C_6$-alkylcarbonyl, $C_1$–$C_6$-alkoxycarbonyl, represent in abbreviated fashion a list of the individual members of the group. All the alkyl, alkoxy, alkylthio, alkenyl and alkynyl moieties can be straight-chain or branched.

Examples of specific meanings are:

— $C_1$–$C_4$-alkyl: methyl, ethyl, n-propyl, 1-methylethyl, n-butyl, 1-methylpropyl, 2-methylpropyl and 1,1-dimethylethyl;

— $C_1$–$C_6$-alkyl: $C_1$–$C_4$-alkyl such as n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

— $C_1$–$C_4$-alkoxy: methoxy, ethoxy, n-propoxy, 1-methylethoxy, n-butoxy, 1-methoxypropoxy, 2-methylpropoxy and 1,1-dimethylethoxy;

— $C_1$–$C_4$-alkylthio: methylthio, ethylthio, n-propylthio, 1-methylethylthio, n-butylthio, 1-methylpropylthio, 2-methylpropylthio and 1,1-dimethylethylthio;

— $C_3$–$C_6$-alkenyl: 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl- 3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl- 4-pentenyl, 1,1-dimethyl-2-butenyl, 1,1-dimethyl- 3-butenyl, 1,2-dimethyl-2-butenyl, 1,2-dimethyl- 3-butenyl, 1,3-dimethyl-2-butenyl, 1,3-dimethyl- 3-butenyl, 2,2-dimethyl-3-butenyl, 2,3-dimethyl- 2-butenyl, 2,3-dimethyl-3-butenyl, 3,3-dimethyl- 2-butenyl, 1-ethyl-2-butenyl, 1-ethyl-3-butenyl, 2-ethyl-2-butenyl, 2-ethyl-3-butenyl, 1,1,2-trimethyl- 2-propenyl, 1-ethyl-1-methyl-2-propenyl and 1-ethyl-2-methyl-2-propenyl;

— $C_3$–$C_6$-alkynyl: 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 4-methyl-1-butynyl, 1-methyl-2-butynyl, 4-methyl- 2-butynyl, 1-methyl-3-butynyl, 2-methyl-3-butynyl, 1-hexynyl, 2-hexynyl, 3-hexynyl, 4-hexynyl, 5-hexynyl, 3-methyl-1-pentynyl, 4-methyl -1-pentynyl, 5-methyl -1-pentynyl, 1-methyl -2-pentynyl, 4-methyl- 2-pentynyl, 5-methyl -2-pentynyl, 1-methyl- 3-pentynyl, 2-methyl -3-pentynyl, 5-methyl -3-pentynyl, 1-methyl-4-pentynyl, 2-methyl-4-pentynyl and 3-methyl-4-pentynyl;

— $C_1$–$C_6$-alkylcarbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 3-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl -1-methylpropylcarbonyl and 1-ethyl-2-methylpropylcarbonyl;

— $C_1$–$C_6$-alkoxycarbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl.

The chlorine-substituted olefins I which can be prepared in a simple manner by the process according to the invention are valuable intermediates for synthesizing dyes, drugs and crop protection agents, especially herbicides and growth regulators, as are described in, for example EP-A 240 659, EP-A 379 911, and DE-A 40 42 194.

EXAMPLE 1

Ethyl 3-(2-chloro-5-nitrophenyl)glycidate [starting material II' ($R^1$=2-chloro-5-nitrophenyl; $R^2$=ethoxycarbonyl)]

27.8 kg (150 mol) of 2-chloro-5-nitrobenzaldehyde were added over the course of 2 hours to a mixture of 60 l of ethanol and 56.7 kg of a 21% by weight solution of sodium ethylate in ethanol (=175 mol of $NaOC_2H_5$) at 20°–25° C., and then 20.4 kg (166.6 mol) of ethyl chloroacetate were added over the course of 1 hour. The mixture was stirred for about 15 hours and then the solid was removed as completely as possible and then dried under reduced pressure (100 mbar) at 40° C. Yield: 87%; melting point 79° C.

EXAMPLE 2

Ethyl α,2-dichloro-5-nitrocinnamate [I; $R^1$=2-chloro- 5-nitrophenyl; $R^2$=ethoxycarbonyl]

11.7 g of 36.89% by weight solution of chloromethylenedimethyliminium chloride hydrochloride (26.2 mmol) in dimethylformamide hydrochloride were dissolved in 15 ml of dimethylformamide. A solution of 6.8 g (25 mmol) of ethyl 3-(2-chloro-5-nitrophenyl)glycidate in 15 ml of dimethylformamide was added dropwise to the resulting solution at 25°–30° C. The mixture was then heated at 80° C. for 4 hours, after which the solvent was removed by distillation under reduced pressure. The residue was washed with 50 ml of water and then recrystallized from 40 ml of ethanol. Yield: 72% (E/Z-isomer ratio=3.4:88.5); melting point 91° C.

EXAMPLE 3

Ethyl α,2-dichloro-5-nitrocinnamate [I; $R^1$=2-chloro- 5-nitrophenyl; $R^2$=ethoxycarbonyl]

15 g (0.15 mol) of gaseous phosgene were passed over the course of half an hour into a mixture of 27.5 g (0.1 mol) of ethyl 3-(2-chloro-5-nitrophenyl)glycidate and 200 ml of dimethylformamide at 50° C. The mixture was then heated at 80° C. for 5.5 hours and subsequently allowed to cool to ~25° C. After removal of the solvent under reduced pressure, the residue was recrystallized from 200 ml of ethanol. The crude product was then washed with water and dried at 40° C. under reduced pressure. Yield: 6% (GC: 98.8 percentage area; E/Z isomer ratio=8.9:80.9); melting point 91° C.

EXAMPLE 4

Ethyl α,2-dichloro-5-nitrocinnamate [I; $R^1$=2-chloro- 5-nitrophenyl; $R^2$=ethoxycarbonyl]

7.1 g (60 mmol) of thionyl chloride were added dropwise over the course of 20 minutes to a solution of 13.6 g (50 mmol) ethyl 3-(2-chloro-5-nitrophenyl)glycidate in 100 ml of dimethylformamide at 100° C. The mixture was stirred at 100° C. for 4 hours and the solvent was removed under reduced pressure. 40 ml of ethanol and 10 ml of water were added to the crude product while still warm, after which the mixture was briefly stirred, then cooled to 0° C. and the solid was removed. The crude product was washed twice with a mixture of 20 ml of ethanol and 20 ml of water each time and subsequently dried at 50° C. under 100 mbar. Yield: 73% (GC: 92.1/5.9 percentage area; E/Z isomer ratio=6.5:82.4); melting point 90° C.

EXAMPLE 5

Ethyl α,2-dichloro-5-nitrocinnamate [I; $R^1$=2-chloro- 5-nitrophenyl; $R^2$=ethoxycarbonyl]

7 g (55 mmol) of oxalyl chloride were added dropwise over the course of 15 minutes to a solution of 13.6 g (50 mmol) of ethyl 3-(2-chloro-5-nitrophenyl)glycidate in 100 ml of dimethylformamide. The mixture was then stirred at 20°–25° C. for 1 hour and subsequently heated at 80° C. for 10 hours. The solvent was then removed under reduced pressure. The residue was stirred in 30 ml of ethanol. After cooling to 0° C., the solid was removed, washed with a little cold ethanol and dried at 50° C. under 100 mbar. Yield: 52% (GC: 97.9 percentage area; E/Z isomer ratio=10.0:74.0); melting point 94° C.

EXAMPLE 6

Ethyl α,2-dichloro-5-nitrocinnamate [I; $R^1$=2-chloro- 5-nitrophenyl; $R^2$=ethoxycarbonyl]

Example 4 was repeated with 8.4 g (55 mmol) of phosphoryl chloride as chlorinating agent. The reaction mixture was heated at 100° C. for 5 hours, after which the solvent was removed under reduced pressure. The residue was stirred with 40 ml of ethanol and then cooled to 0° C., and the solid was removed, washed twice with 40 ml of water each time and finally dried under reduced pressure (100

EXAMPLE 7

Ethyl α-chloro-3-nitrocinnamate [I; $R^1$=3-nitrophenyl; $R^2$=ethoxycarbonyl]

A solution of 23.7 g (0.1 mol) of ethyl 3-(3-nitrophenyl)glycidate in 50 ml of dimethylformamide was added dropwise over the course of 15 minutes to a mixture of 14.1 g (0.11 mol) of chloromethylenedimethyliminium chloride and 150 ml of dimethylformamide. The mixture was stirred at 20°–25° C. for 1 hour and then at 80° C. for 2.5 hours, after which the solvent was removed under reduced pressure. The residue was stirred with 50 ml of ethanol and, after cooling to –10° C., the solid was removed, washed with a little cold ethanol and dried at 50° C. under 100 mbar. Yield: 34% (GC: 99.6 percentage area; pure Z isomer); melting point 75° C.

EXAMPLE 8

Ethyl α,2-dichloro-5-nitrocinnamate [I; $R^1$=2-chloro-5-nitrophenyl; $R^2$=ethoxycarbonyl]

31.79 g (0.405 mol) of acetyl chloride were added dropwise over the course of 25 min to a mixture of 66 g (0.225 mol) of ethyl 3-(2-chloro-5-nitrophenyl)glycidate (purity 92.6%), 11.93 g (0.113 mol) of sodium carbonate and 131.2 g (1.797 mol) of dimethylformamide at 100° C. After stirring at 20°–25° C. for 6 h, the solids were removed and then the resulting solution was concentrated at not above 64° C. under 10 mbar. The residue was washed with 30 ml each of ethanol, water and petroleum ether and was dried at 50° C. under reduced pressure to give a pale brown solid. Yield: 68% (GC: 95.2 percent area).

200 MHz, $^1$H-NMR (in $CDCl_3$; TMS as internal standard): δ [ppm]=1.42 (t, 3H, $CH_3$); 4.42 (q, 2H, $CH_2$); 7.62 (d, 1H, aromatic); 8.10 (s, 1H, CH); 8.21 (dd, 1H, aromatic); 8.82 (d, 1H, aromatic).

We claim:

1. A process for preparing chlorine-substituted olefins of the formula I

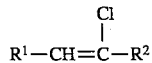

where $R^1$ is a C-organic radical and $R^2$ is one of the following groups: —CN, —CO—$R^3$, —CO—S—$R^3$, —CO—O—$R^3$ or —CO—$NR^4R^5$, where $R^3$ is a C-organic radical and $R^4$ and $R^5$ are each hydrogen or a C-organic radical, which comprises reacting an oxirane of the formula II

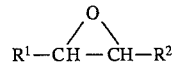

in the presence of a carboxamide (IIIa)

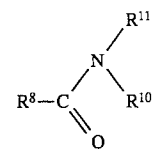

where the substituents have the following meaning:
  $R^8$ is hydrogen, $C_1$–$C_6$-alkyl or phenyl and
  $R^{10}$ and $R^{11}$ are each $C_1$–$C_6$-alkyl or phenyl or
  $R^{10}$ and $R^{11}$ form, together with the common nitrogen atom, pyrrolidinyl, piperidinyl or morpholinyl;
or a lactam IIIb

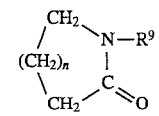

where n is 0, 1 or 2 and $R^9$ is $C_1$–$C_6$-alkyl or phenyl in liquid phase with a chlorinating agent.

2. A process as defined in claim 1, wherein a Vilsmeier salt or a non-oxidizing chlorinating agent is used as the chlorinating agent.

3. A process as defined in claim 2, wherein sulfuryl chloride, thionyl chloride, acetyl chloride, benzoyl chloride, pivaloyl chloride, bis(trichloromethyl) carbonate, oxalyl dichloride, phosphorus oxychloride, phosphorus trichloride, phosphorus pentachloride, methanesulfonyl chloride, chlorosulfonic acid, trichloromethyl chloroformate or phosgene is used as the non-oxidizing chlorinating agent.

4. A process as defined in claim 1, wherein an inert solvent is used in addition to IIIa or IIIb.

5. A process as defined in claim 1, wherein $R^1$ is an aromatic or heteroaromatic radical.

6. An oxirane of the formula IIa

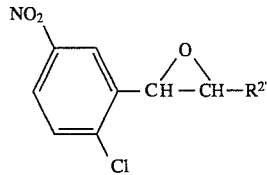

where $R^{2'}$ is cyano, $C_1$–$C_6$-alkylcarbonyl, $C_1$–$C_6$-alkoxycarbonyl or $C_1$–$C_6$-alkylthiocarbonyl.

* * * * *